(12) United States Patent
Ramesh et al.

(10) Patent No.: US 11,610,466 B2
(45) Date of Patent: *Mar. 21, 2023

(54) MULTILEVEL RAPID WARNING SYSTEM FOR LANDSLIDE DETECTION

(71) Applicant: Amrita Vishwa Vidyapeetham, Coimbatore (IN)

(72) Inventors: Maneesha Vinodini Ramesh, Kollam (IN); Divya Pullarkatt, Ernakulam (IN); Hemalatha Thirugnanam, Kollam (IN); Nitin Kumar M., Ernakulam (IN); P. Venkat Rangan, Coimbatore (IN)

(73) Assignee: Amrita Vishwa Vidyapeetham

( * ) Notice: Subject to any disclaimer, the term of this patent is extended or adjusted under 35 U.S.C. 154(b) by 0 days.

This patent is subject to a terminal disclaimer.

(21) Appl. No.: 17/509,734

(22) Filed: Oct. 25, 2021

(65) Prior Publication Data

US 2023/0046111 A1    Feb. 16, 2023

(51) Int. Cl.
| | |
|---|---|
| G08B 21/10 | (2006.01) |
| G08B 21/18 | (2006.01) |
| G01V 1/00 | (2006.01) |
| G01N 33/24 | (2006.01) |
| G01V 1/18 | (2006.01) |
| G01W 1/14 | (2006.01) |
| G01V 1/02 | (2006.01) |

(52) U.S. Cl.
CPC ........... *G08B 21/10* (2013.01); *G01N 33/246* (2013.01); *G01V 1/008* (2013.01); *G01V 1/159* (2013.01); *G01V 1/181* (2013.01); *G01W 1/14* (2013.01); *G08B 21/182* (2013.01)

(58) Field of Classification Search
CPC .... G08B 21/10; G08B 21/182; G01N 33/246; G01V 1/008; G01V 1/159; G01V 1/181; G01W 1/14
USPC .......................................................... 340/690
See application file for complete search history.

(56) References Cited

U.S. PATENT DOCUMENTS

| | | | | |
|---|---|---|---|---|
| 6,119,535 A | * | 9/2000 | Tambo ................... | G01F 23/243 73/865.8 |
| 6,530,284 B1 | * | 3/2003 | Tambo ................... | G01F 23/243 340/690 |
| 6,661,346 B1 | * | 12/2003 | Wood ..................... | G08B 21/10 73/594 |
| 8,692,668 B2 | * | 4/2014 | Ramesh ................. | G01V 1/008 340/539.22 |
| 9,262,124 B2 | * | 2/2016 | Mello ................ | G06Q 10/0635 |

(Continued)

*Primary Examiner* — Zhen Y Wu
(74) *Attorney, Agent, or Firm* — Donald R. Boys; Central Coast Patent Agency LLC

(57) ABSTRACT

A hierarchical early-warning system for landslide probability issues a first level warning based on measured rainfall amounts exceeding a determined threshold, a second level warning, after the first level warning, based additionally on measured soil moisture content measured at different levels, and Factor of safety derived from forecasted pore pressure (FPP) each exceeding a determined threshold, a third level warning, after the first and the second level warnings, based additionally on ground movement measurements compared to a determined threshold, and a fourth level warning after the first, second and third level warnings, based additionally on data from movement-based sensors including strain gauge data.

8 Claims, 12 Drawing Sheets

(56) References Cited

U.S. PATENT DOCUMENTS

| | | | | |
|---|---|---|---|---|
| 10,719,778 | B2* | 7/2020 | Ochiai | G01V 1/008 |
| 10,762,774 | B2* | 9/2020 | Tsunoda | G08B 21/10 |
| 2003/0184445 | A1* | 10/2003 | Chen | G08B 21/10 |
| | | | | 340/690 |
| 2012/0206258 | A1* | 8/2012 | Ramesh | G08B 21/10 |
| | | | | 340/539.22 |
| 2014/0116320 | A1* | 5/2014 | Curiel | G10K 1/07 |
| | | | | 116/200 |
| 2014/0159915 | A1* | 6/2014 | Hong | H04Q 9/00 |
| | | | | 340/870.07 |
| 2015/0331143 | A1* | 11/2015 | Han | G06F 30/00 |
| | | | | 702/5 |
| 2018/0045853 | A1* | 2/2018 | Kirschbaum | G01W 1/14 |
| 2018/0252694 | A1* | 9/2018 | Mase | G08B 31/00 |
| 2020/0375016 | A1* | 11/2020 | Hutson | H05B 47/22 |
| 2022/0260737 | A1* | 8/2022 | Kuwamori | G01V 1/306 |

* cited by examiner

MULTILEVEL RAPID WARNING SYSTEM FOR LANDSLIDE DETECTION

CROSS REFERENCE TO RELATED APPLICATIONS

The present application claims priority to India Patent Application 202141037092 filed 16 Aug. 2021. All disclosure of the parent case is incorporated herein at least by reference.

BACKGROUND OF THE INVENTION

1. Field of the Invention

The present invention is in the field of disaster preparedness and pertains particularly to methods and apparatus for monitoring landslide prone areas and predicting impending landslides before they occur.

2. Description of Related Art

In the field of disaster preparedness relative to landslides and avalanches there are conventions and methods for assessing dangerous conditions and providing warnings if possible, to potentially affected communities of impending landslides or similar events that involve displacement of earth or in the case of avalanche, snow. A challenge with monitoring landslide conditions is that more often singular and isolated sensors are checked periodically along with visual presence assessments to determine the potential risks of a landslide and there is not enough of or the right kind of sensor data to enable an accurate and timely prediction of an impending event.

Alerts and warnings associated with potential landslides are often issued when rainfall amounts are high, but no other significant data is collected and analyzed prior to and during a landslide event that would enable logical prediction of the course and intensity of a potential slide. Typically, once rainfall amounts reach a certain level, a generic landslide warning may be issued based on past events or educated guessing as to the timing and severity of the event.

Therefore, what is clearly needed is a system and methods for deploying and monitoring a variety of strategically placed sensors accessible through an alert-based monitoring and notification network that is regionally deployable and accessible to those potentially affected by the monitored local events, and that issues warnings in increasingly urgent situations.

BRIEF SUMMARY OF THE INVENTION

In an aspect of the invention a hierarchical early-warning method for landslide probability is provided, comprising issuing a first level warning based on measured rainfall amounts exceeding a determined threshold, issuing a second level warning, after the first level warning, based additionally on measured soil moisture content measured at different levels, and Factor of safety derived from forecasted pore pressure (FPP) each exceeding a determined threshold, issuing a third level warning, after the first and the second level warnings, based additionally on ground movement measurements and measured pore pressure values compared to a determined threshold, and issuing a fourth level warning after the first, second and third level warnings, based additionally on data from movement-based sensors including strain gauge data.

In one embodiment of the method, in the determination of the first level warning, a global and a regional threshold are determined and compared to measured rainfall intensity. Also in one embodiment, in the determination of the first level warning, rainfall intensity per hour and for antecedent durations of 1 day, 3 days, 5 days, 7 days and 15 days are determined, threshold values for each of these durations are determined for a global model and a regional model, and comparison of intensity to threshold is made for each model, and the first level warning is issued if either threshold is exceeded. In one embodiment, in determination of the second level warning, threshold values are determined for progressively longer durations from one hour to fifteen days. And in one embodiment, in determination of the second level warning, a Factor of Safety (FoS) value, indicating stability of a slope in consideration, is calculated based in part on forecasted pore pressure, and Volumetric Water Content (VWC) is measured using soil moisture sensors, and the second level warning is issued if VWC is equal to or greater than one, meaning the soil is saturated, AND FoS is less than one, meaning the slope is unstable.

In one embodiment of the method, in determination of the second level warning, a site-specific rainfall threshold is determined to have been exceeded, in addition to thresholds for pore pressure and moisture content. Also, in one embodiment determination of the second level warning requires site-specific rainfall to have exceeded the threshold continuously for a period of at least 'T' days. In one embodiment, in determination of the third level warning, ground movement measurements include vibration intensity. In one embodiment, wherein, in determination of the third level warning, four logical paths are followed in parallel, a first considering expected tiltmeter data compared to a set threshold, a second considering geophone data and soil properties, a third considering rainfall intensity compared to site-specific threshold for time of 'T' days, and a fourth considering measured pore pressure. And in one embodiment, in determination of the fourth level warning, four parallel logical paths are followed, a first path comparing rainfall intensity to site-specific threshold, a second path based on measured tiltmeter data, measured strain gauge data and soil properties, a third path based on geophone data and soil properties, and a fourth path based on pore pressure and location-specific weighted threshold values. In various embodiments, issuing the first level warning, second level warning, third level warning, or fourth level warning, comprises actuating one or more of an email message, an SMS, a flashing light, or a voice alarm.

DETAILED DESCRIPTION OF THE INVENTION

Figure 1:
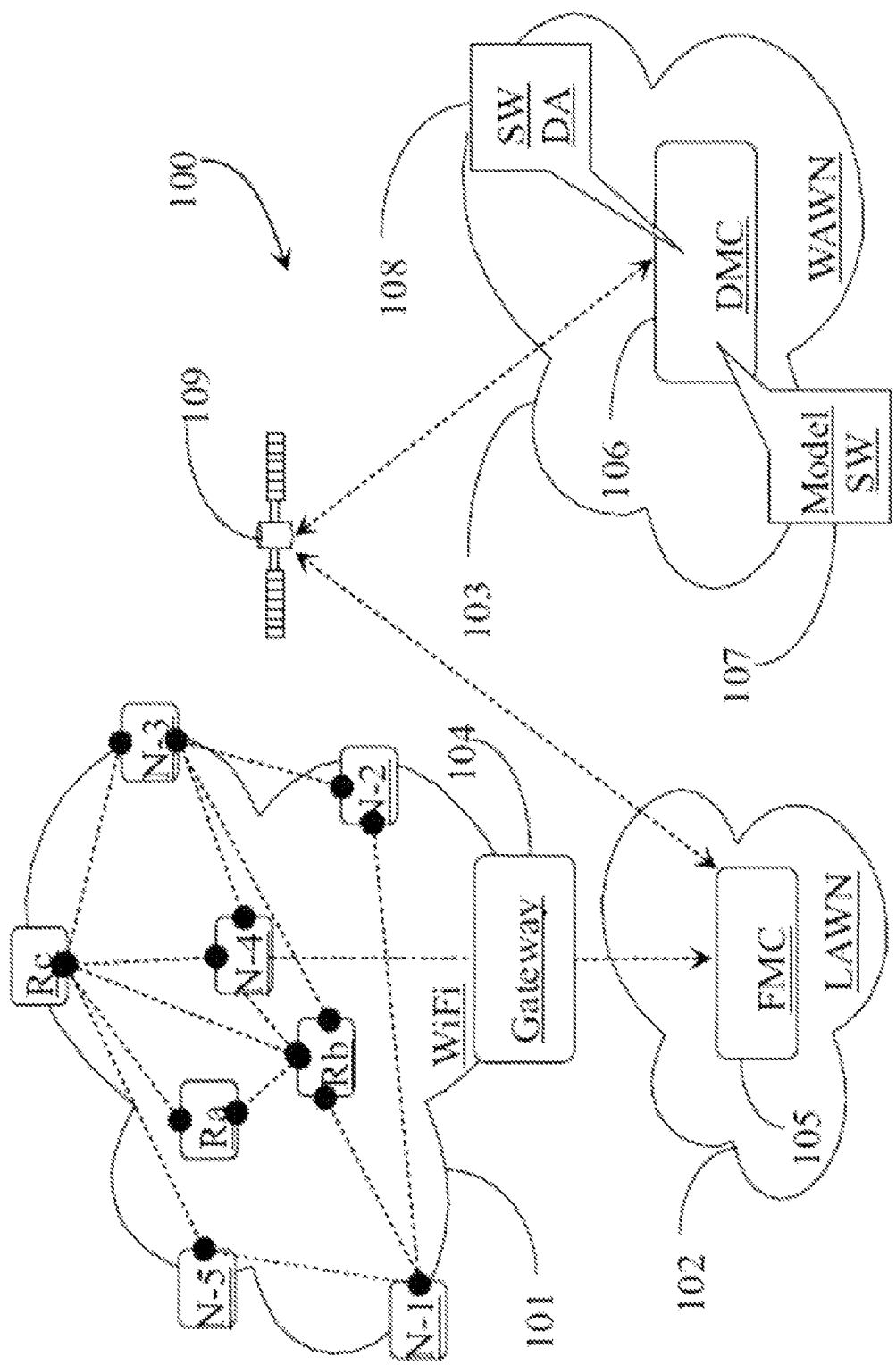
FIG. 1 is an architectural diagram illustrating a communications network supporting landslide event monitoring according to an embodiment of the present invention.

While the invention has been disclosed with reference to certain embodiments, it will be understood by those skilled in the art that various changes may be made and equivalents may be substituted without departing from the scope of the invention. In addition, many modifications may be made to adapt to a particular situation or material to the teachings of the invention without departing from its scope.

Throughout the specification and claims, the following terms take the meanings explicitly associated herein unless the context clearly dictates otherwise. The meaning of "a", "an", and "the" include plural references. The meaning of "in" includes "in" and "on." Referring to the drawings, like numbers indicate like parts throughout the views. Additionally, a reference to the singular includes a reference to the plural unless otherwise stated or inconsistent with the disclosure herein.

The inventors provide a wireless node and sensor array connected to an alerting network for monitoring a landslide-prone area for signs of an impending landslide, and for alerting affected communities of an impending landslide event, using the rapid warning method illustrated herein. The present invention is described in enabling detail using the following examples, which may describe more than one relevant embodiment falling within the scope of the present invention.

FIG. 1 is an architectural diagram illustrating a communications network 100 supporting landslide event monitoring and event notification according to an embodiment of the present invention. Communications network 100 includes a wireless fidelity network (WiFi) 101 accessible through a wireless gateway 104. Network 101 is termed a field network and may be one of several such networks deployed in one or more areas of ground that may be prone to landslide activity. Typically speaking, a landslide prone area will comprise a sloping grade that may become unstable during heavy rain. Network 101 may be a heterogeneous communication network consisting of WiFi, ZigBee, cellular, etcetera.

Field network 101 may also be termed a probe network in this specification because of deployment of deep earth probes (not illustrated) that carry various geologic and hydrologic sensors that report rain, pore-pressure saturation and earth movements during monitoring of a landslide event. In this embodiment there are three rain gauges deployed in the area covered by field network 101. These are rain gauges Ra, Rb, and Rc. In a typical implementation, a rain gauge is deployed near the top or crown area of a slope that is prone to landslide activity. Another rain gauge is typically placed near the middle of the slope and the third gauge near the foot or toe of the slope. In this embodiment, rain gauges are the first line of sensors used to determine when a slope should be monitored and at what frequency sensor reporting is commenced.

In this embodiment, several wireless nodes, N1-N5 are deployed throughout the suspect area within the communication range of the wireless network. In this example field network 101 is a WiFi/Zigbee/Cellular/LoRa network, however, other wireless network technologies might be used to create a local wireless network. A wireless node is the reporting node for at least one deep earth probe (not illustrated) deployed adjacent to or at least in close proximity to the host wireless node for efficiency in sensor reporting. Each wireless node may send and receive data from other sister nodes in the network and each of the nodes has access to information from rain gauges Ra, Rb, and Rc. In one embodiment, each rain gauge includes a wireless transceiver for reporting rainfall amounts to the other wireless nodes connected to deep earth probes used to deploy the various sensors. Each wireless node includes a transceiver and can send data out to an external network as well as receiving data such as commands from the external network. The hardware platforms incorporated include Crossbow MicaZ, WINSOC wireless sensor nodes, and Amrita IoT nodes to capture the prevailing meteorological, geological and hydrological parameters.

Gateway 104 may support several field or "probe" networks. Gateway 104 is connected to a local area wireless network (LAWN) 102. A WiFi network (not specifically illustrated) is established between gateway 104 and a field management center (FMC) 105 to support LAWN 102. A network controller (not illustrated) is deployed between probe network gateway 104 and FMC facility 105. The network controller supports WiFi protocols such as 802.11b and 802.11g as well as transmission control protocol (TCP) data packets and user data gram protocol (UDP) data packets. In one embodiment, FMC is automated. However, there may be one or more individuals located at the site that perform routine duties.

FMC 105 is established some 500 meters or so from the field network 101. FMC 105 includes, among other things, a data acquisition (DAQ) controller that receives data from rain gauges and specified geo-sensors that are deployed in the field network 101. FMC 105 also includes a database (DB) server and a field network controller. The field network controller supports network protocols like broadband and general packet radio service (GPRS). The field network controller supports a very small aperture terminal (VSAT) ground terminal that connects network 102 via a satellite 109 to a wide area wireless network (WAWN). It is noted herein that the described network components that are not specifically illustrated in this example are well known network components that are available to the inventors.

WAWN 103 may be any type of wireless digital network including a municipal area network (MAN) or any wireless Internet segment. WAWN 103 provides wide area connectivity, and it consists of satellite network, a global system for mobile/general packet radio service (GSM/GPRS) network, and broadband network. WAWN 103 includes a data management center (DMC) 106. DMC 106 includes among other things, a central management gateway through which data are propagated, a database, and web server for serving web-based alerts. Various alert services may be provided such as alerts via email, short message services (SMS), and multimedia message services (MMS). In one embodiment, telephony-based alert services may also be provided such as a reverse 911 calling center or dispatch services. It is noted herein that components within DMC 106 that are not illustrated in this example are well known in the art and available to the inventor.

DMC 106 includes a landslide modeling software application 107 and raw data analysis software 108. Landslide modeling software 107 enables knowledge workers monitoring local rain events to determine the proper thresholds of data coming into the center from the sensors deployed in the fields. Changing certain parameters of the landslide model 107 can result in the adjustment of certain thresholds relative to sensor data that when breached would result in a notification, alert, or warning of an impending landslide. Of course, the goal of the deployment network 101 is to enable more time for affected communities to evacuate from an area that will be devastated by a slide. Data analysis software 108 is provided to analyze incoming sensor data in real time and to determine when the data indicates certain stages of alert.

Under extreme conditions, WAWN 103 adapts if part of the available network is compromised. For example, if the VSAT network is not available, the broadband or GPRS connectivity supported by FMC 105 is used for uploading the sensor data in real time directly to a web page with minimum delay and thus provides fault tolerance. The real time data and the results of the data analysis may be streamed over the Internet in real time. Alert services such as E-Mail, SMS and MMS are implemented to alert about the probability of landslides, status of the network, and for monitoring the system components.

The network architecture illustrated in this example is scalable. Any number of wireless nodes and additional landslide deployment fields can be incorporated via a Wi-Fi network to the same FMC (105). This gives scientists and emergency notification personnel the capability of monitoring very large areas of landslide concern. Moreover, the spatio-temporal analysis relative to a larger region as opposed to a local pocket provides an even better understanding of events that trigger landslides.

Network 100 delivers data continuously from a set of deep earth probes deploying various sensors in what may be a remote mountainous area to a data management, analysis, and visualization center, which might be hundreds of miles distant from the monitored area. Therefore, a very lightweight management framework (LMF) is provided that incorporates different heterogeneous networks such as 802.15.4, 802.11b/g, VSAT, GPRS, GSM, Internet, and other proprietary wireless sensor network and hardware architectures. It can handle various network failures, data corruption, packet loss, and congestion problems. More detail regarding network components such as data handlers, data caches, and so forth is illustrated in the provisional patent application that this specification has priority to. These include various power consumption and data handling optimizations to make reporting and alerting more efficient than would otherwise be the case.

Figure 2:
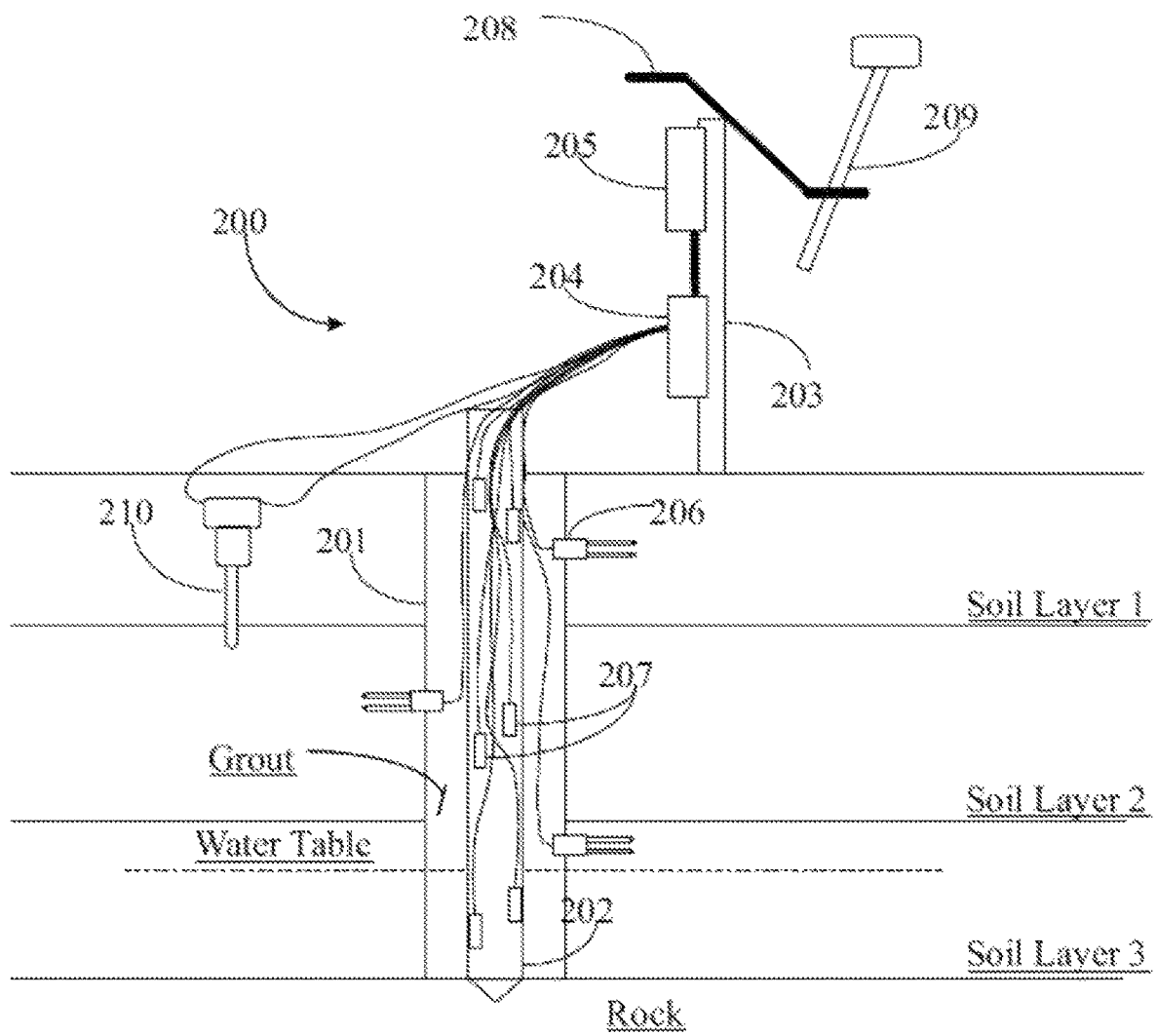
FIG. 2 is an elevation view of a wireless node with hydrologic and geologic sensor deployment in a landslide prone area.

FIG. 2 is an elevation view of a wireless node 200 with hydrologic and geologic sensor deployment in a landslide prone area. In this example, the term wireless node shall incorporate all of the connected components and sensors including the data acquisition board, power source, and wireless transceiver. Wireless node 200 includes one or a set of deep earth probes (DEP) such as a DEP 202 that is placed in a prepared borehole 201 that is drilled into the earth through at least three soil layers. DEP 202 comprises a tubular probe body that may be of different length and diameter dependent on the type of sensors that will be attached to it or otherwise deployed by it.

Borehole 201 may include one or more than one deep earth probe that has sensors attached thereto or deployed therein. In this example, probe 202 is anchored in bedrock below three different successive layers of soil (for illustration purposes). The properties of each of these layers are different, so it is important to collect hydrologic and geologic data from each of the layers. These are a soil layer 1, a soil layer 2, and a soil layer 3. In one embodiment, criteria for drilling a deep earth probe borehole is that it be drilled through at least three disparate soil layers and culminate at the bedrock layer or other layer of rock. Using these criteria, the length of the borehole may vary greatly.

In actual practice in the deployment field, the borehole is continued until bedrock is determined. In specific situations when the bedrock is too deep under the surface of the earth or about 100 meters, specific criteria determined the point that drilling could be stopped. The termination of the borehole occurred after finding (a) More than three separate impermeable layers of soil; (b) Weathered rock for more than 5 meters; or (c) Water table and weathered rock for more than 5 meters.

In this example, the water table is illustrated as a broken line just below soil layer 2. An impermeable soil layer has the potential to hold a perched water table. Such a water table may become overwhelmed during a heavy rain event and may contribute to a landslide. Therefore, the water table plays an important role in landslide monitoring as does saturation levels of the different soil layers. In this example, probe 202 has multiple strain gauges 207 attached thereon facing the expected direction of soil movement should it occur during a landslide. A strain gauge measures pressure against itself caused by abutment of adjacent earth. It is a geologic sensor that may detect minute movement of soil. In this example, strain gauges are strategically located near the top, middle, and near the nose of deep earth probe 202. The soil layer movements are generally initiated above the impermeable layers of soil. The strain gauge sensors are deployed in the impermeable layers and the layer above the impermeable layer to measure the strain variation experienced in the impermeable layer and the layer above it.

In one embodiment, multiple strain gauges 207 are deployed in each of the soil layers to capture the soil movement in x, y directions. According to the risk level of the impermeable layer, the location of the sensor placement, and the prospective landslide initiation and direction of flow, the number of sensors and the direction of the deployment are determined using an algorithmic formula. Strain gauges are connected by sensor wire to a wireless transceiver 204 equipped with a data acquisition board (DAQ) board 204 that is connected by cable to a hybrid battery-charging unit 205. In this example, wireless transceiver 204 and charging unit 205 are mounted on a post 203 adjacent to the borehole.

A geophone sensor 210 is illustrated in this example in soil layers 1 and 2. A geophone measures earth movement in the soil layer and is a geologic sensor. Geophone 210 is connected to wireless transceiver 204 by sensor wiring. There may be several geophones connected to transceiver 204 without departing from the spirit and scope of the present invention. In one embodiment, hydrologic sensors are the first sensors that are monitored for data during a rain event that is strong enough to warrant landslide monitoring.

In this example, several dielectric moisture sensors 206 are deployed at various levels in the walls of borehole 201. A dielectric moisture sensor measures the amount of moisture in the soil layer where it resides. It is important to collect data from each successive soil layers above the water table. A grout mix (Grout) is prepared and packed into the borehole to compensate for soil removed from the hole. The grout mix is used to achieve the same soil strength and compactness inside the borehole that the normal soil would have. This mix is prepared by using a predetermined ratio of water, bentonite, and cement. In optional configurations, wireless node 200 may include a solar panel 208 for additional charging power. Also optional is an external wireless antenna 209 for improving wireless signal.

Figure 3:
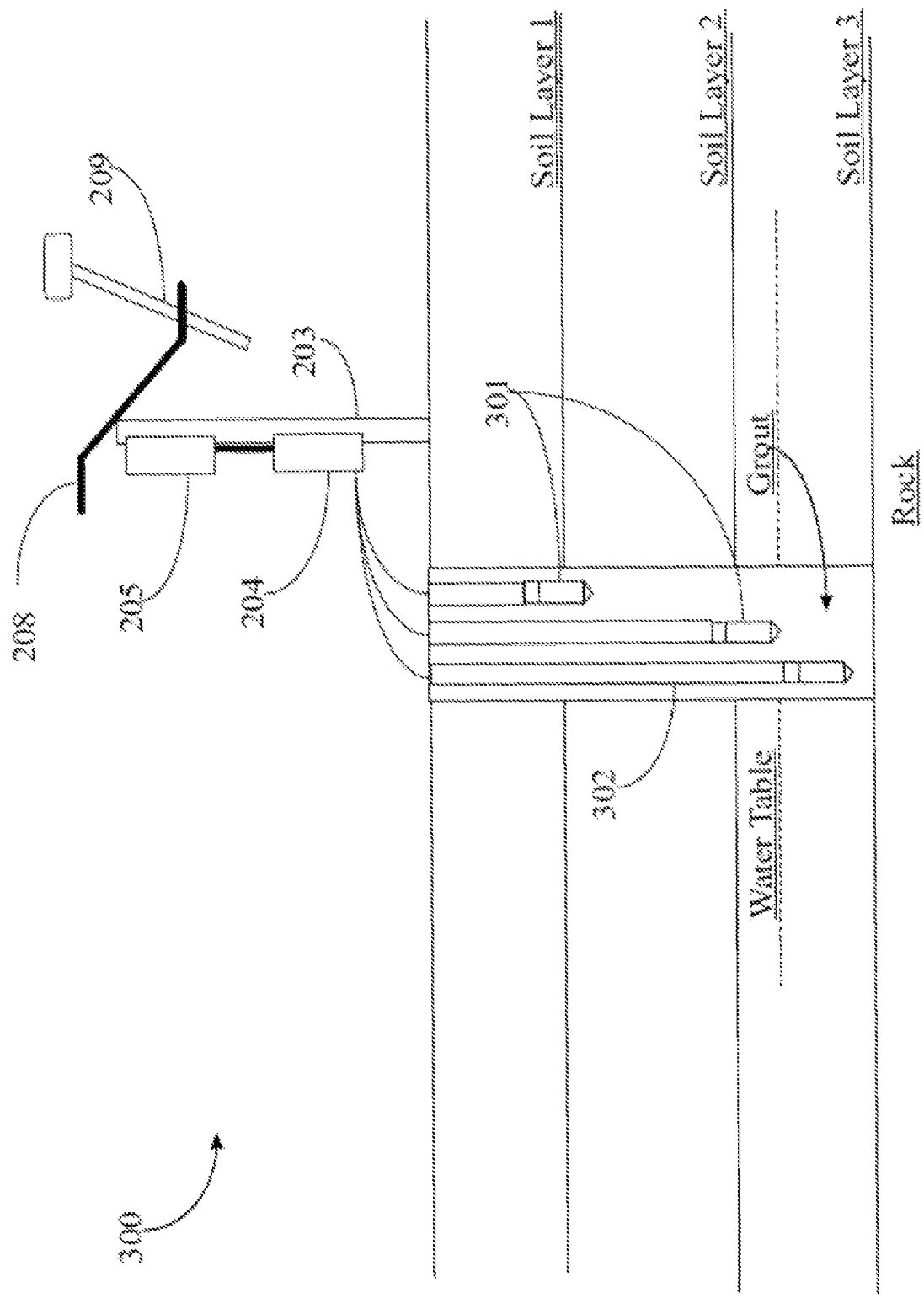
FIG. 3 is an elevation view of a wireless node with alternative hydrologic sensor deployment in a landslide prone area.

FIG. 3 is an elevation view of a wireless node 300 with alternative hydrologic sensor deployment in a landslide prone area. Wireless node 300 includes some of the same components described previously such as wireless transceiver 204, charging unit 205, solar panel 208 and antennae 209 all mounted on post 203. In this particular embodiment, there are three deep earth probes 302 inserted into the borehole at different soil layer depths. These particular probes have probe bodies that are smaller in diameter than those carrying other sensor types. These DEPs 302 are adapted to carry piezometers 301. A piezometer is a hydrologic moisture sensor adapted to test water pressure (pore pressure) at various soil levels within the borehole. Each piezometer is attached to a separate deep earth probe 302 and is positioned by the probe in the borehole at a particular soil layer. In this example the piezometers are in a nested configuration with one at the boundary of soil layer 1 and soil layer 2; another at the boundary of soil layer 2 and soil layer 3 just above the water table; and another below the water table in soil layer 3.

The piezometers will measure the water pressure (pore pressure) within the borehole at various layers of soil. Nested piezometers are placed below and above the water table to monitor the variation of pressure levels according to the climatic condition. In addition, they are deployed in the impermeable layers of the soil because water tables will accumulate above the impermeable soil layers leading to slope instability. In practice, the hydrologic gauges that can be deployed with a deep earth probe and or wireless node are rain gauges, dielectric moisture sensors and piezometers. These are the first line sensors that are monitored to determine if geologic movement sensors need to be powered on and monitored for data. As in other embodiments, the boreholes are backfilled with a grout composition to fill space not occupied by a DEP so soil properties, like compactness for example, are mimicked by the grout mixture.

Figure 4:
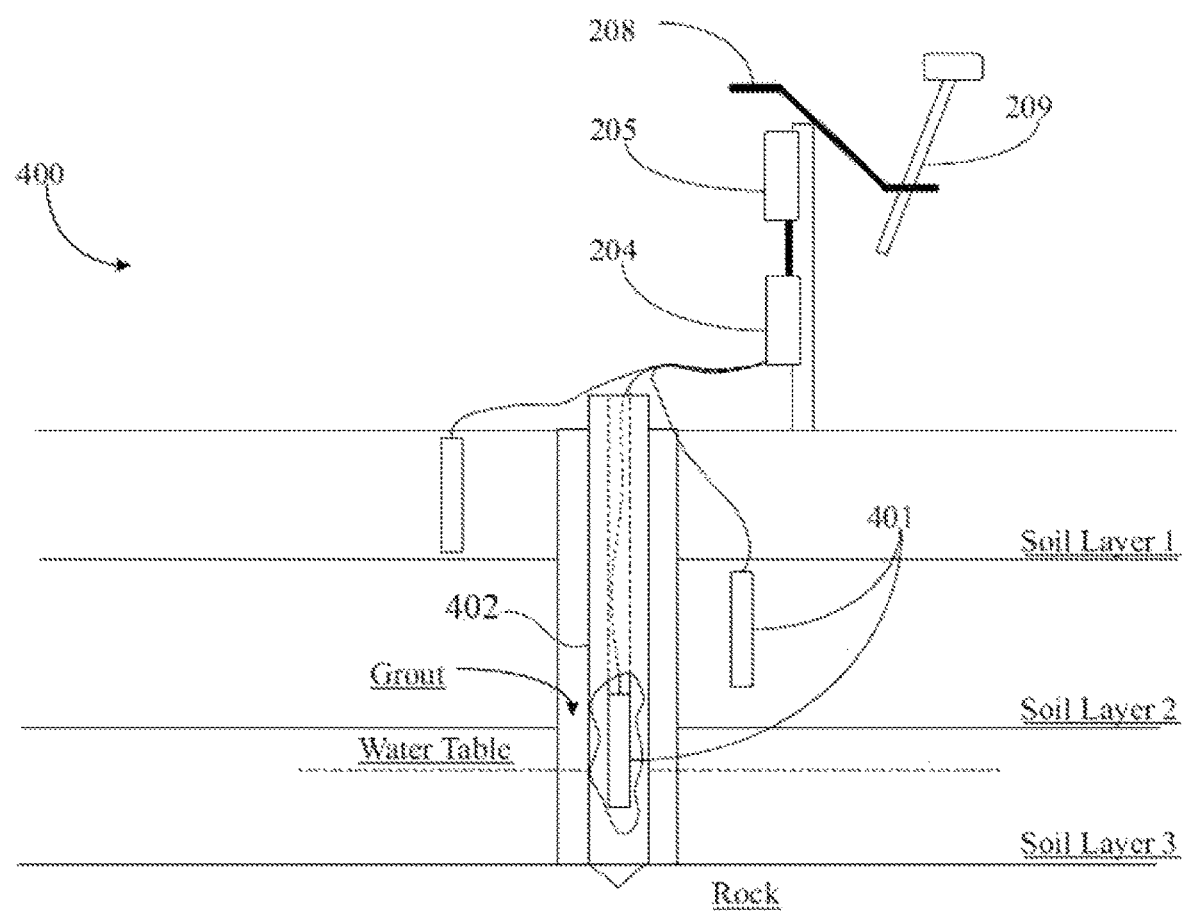
FIG. 4 is an elevation view of a wireless node and geological sensor deployment in a landslide prone area.

FIG. 4 is an elevation view of a wireless node 400 and geological sensor deployment in a landslide prone area. In this example, wireless node 400 includes a deep earth probe 402 that is carrying a tiltmeter 401. Tilt meters 401 are also deployed in the soil layers above the water table. Multiple tiltmeters are deployed to measure the angle of tilt experienced by the soil layers during the pre-initiation or at initiation of a landslide event. The soil layer movements are mostly initiated above the impermeable soil layer. The tiltmeter sensors are deployed in the impermeable layers and the permeable layer or layers above the impermeable layer to measure the angle of deformation experienced in the impermeable layer and the layers above it.

In this example, a tiltmeter 401 is fixed inside a DEP 402. Only part of the sensor tube will move as the slope slowly deforms because of the DEP's length and due to the fact that the DEP is anchored in the solid weathered rock or bedrock below the soil. This will cause part of the tube to become bent. The tiltmeter measures this bend in the tube. Trigonometric formulas may then be applied in raw data analysis to determine the amount of movement of the slope that has occurred. The sensor tube movement is very slight. Ground velocities in the range of millimeters per hour are detected. Wireless node 400 includes wireless transceiver 204, charging unit 205, solar panel 208 and antennae 209.

In one embodiment all 6 sensor types comprising both geologic and hydrologic sensors described thus far in this specification are deployed in a same bore hole by a set of appropriate deep earth probes. The hydrologic sensors represent the first line of sensors monitored for data followed by the geologic sensors if thresholds associated with the hydrologic sensors are breached.

Frequency of measuring each of the sensors (in one DEP): Specific optimizations are implemented in the data collection network in order to reduce redundancy in data collection and to optimize energy use by the network. One example of redundant data might be data collected at times of low landslide risk where little or no rain is falling, and sensor data is largely static or unchanging. During this time, the sampling rate of the sensors may be significantly reduced. Likewise, hydrologic sensors are powered on and monitored first until there is a requirement for powering up and monitoring geologic sensors. At heavy rainfall periods, sensor values will change more rapidly. Therefore, data has to be collected at a much higher frequency. Two basic approaches or methodologies are provided to address these issues.

Threshold Based Temporal Data Collection: One approach provided is to continuously monitor all of the deployed sensors in constant periodic intervals. In this embodiment, the frequency of sensor monitoring changes with environmental conditions on the ground. The frequency of measurement increases when the rainfall rate increases. In a variation of this aspect, a tri-level threshold approach is practiced. The levels correlate to low, medium, and high rainfall thresholds. When the threshold rate of rainfall (measured by rain gauges) crosses a low threshold the frequency of sensor measurement will increase proportionately. As long as the rainfall rate continues to be in the same range of measurement, the frequency of sensor sampling and measurement will not change. This approach is threshold based temporal data collection and aggregation technique. The frequency of sensor data collection increases with each level breached by the rainfall amount as measured by the rain gauges. It is noted herein that at some point in this process all of the sensors may be powered on and data collection might be continuous at critical rainfall levels.

The rain gauge reading of the rate and duration of rainfall determines the alert level of the network in this example and if a transition from one alert level to another is required. The network remains in a low level of alert if the deployment site receives zero to X mm of rain. This amount might be averaged over the number of rain gauges deployed in the field. If rainfall amounts increase to a level above the first pre-determined threshold, the network will transition to medium alert. The exact threshold amounts (X) may be adjusted depending on historic rainfall patterns. The network will transition from medium to high alert, if the rainfall rate increases above the next pre-determined threshold level. Pre-determined rainfall rate thresholds will be modified after analyzing the historic rainfall data for the past few years collected from the real-time system, in order to account for the variations in climatic conditions also. The aggregation technique used in this embodiment is to average the sensor values and transmit them when the new data overshoots the pre-determined threshold value for each of two or more alert states. In this case the data between disparate sensors are not aggregated together. The data aggregation technique for each sensor is performed separately.

Sensor Triggered Measurement Initiation: In this embodiment specific ones of the deployed sensors with a wireless node are powered on and monitored first during low risk periods. In these periods only the rain gauges are on and collecting data. In one example, the rain gauges, dielectric moisture sensors and piezometers are all powered on and are collecting data during low risk periods. Generally speaking, the hierarchy might be rain gauges first, then moisture sensors, and then piezometers. When the data received from the piezometer sensors cross the low threshold (averaged across the sensors) it will initiate data collection from the strain gauges, tilt meters, and geophones, which all detect earth movement. The data collection from all the sensors will continue, once the moisture sensor becomes saturated. The frequency of measurement may also be increased. In the same manner once the piezometers are saturated, the frequency of the sensor measurement will be increased up to continuous measurement if required. This will reduce the energy consumption by only employing and collecting data from the sensors that are then required. It might be noted that rain gauges are always working in the system. The aggregation technique used in the DEP that has adopted sensor triggered measurement initiation technique has aggregated related sensors to derive the correlation between their sensor data. These data will be forwarded to the higher layer sensor nodes. So the amount of data transmitted will be less and the processing time will be reduced.

Figure 5:
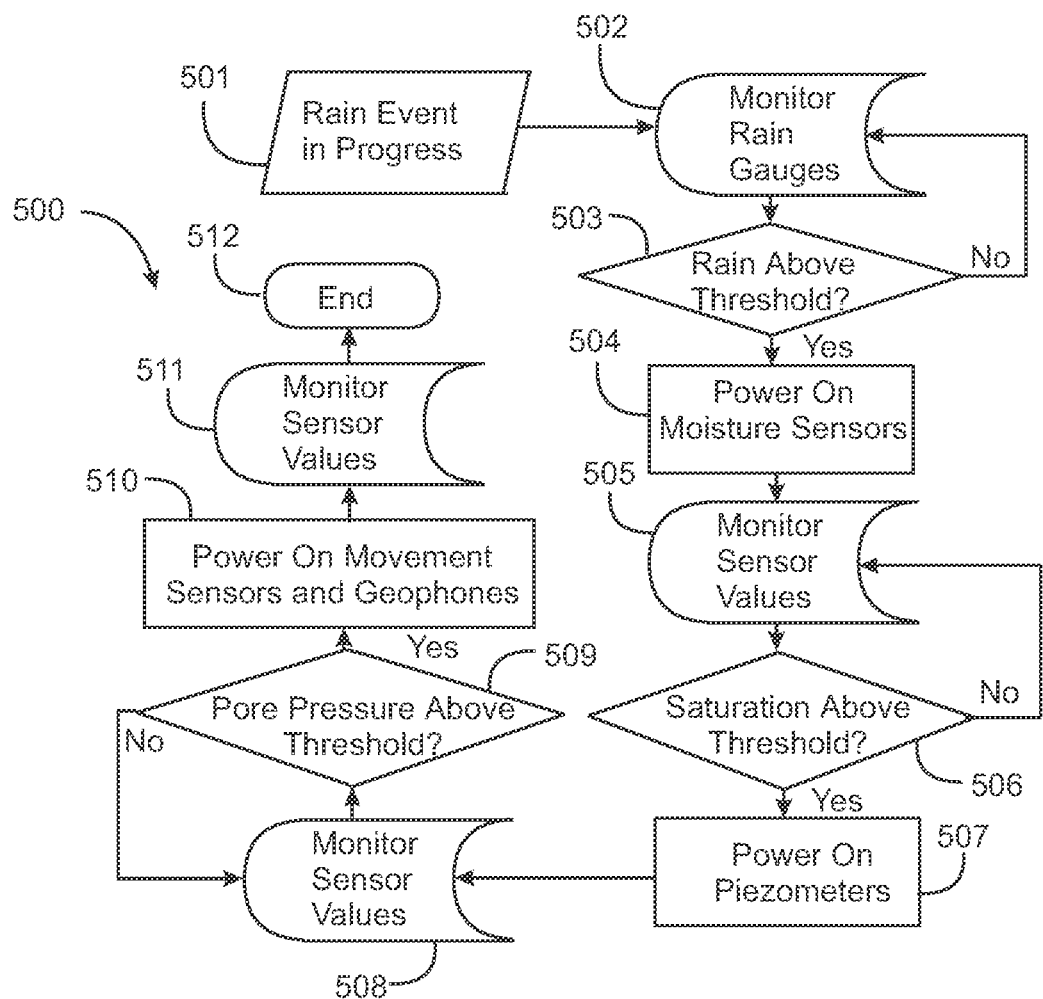
FIG. 5 is a process flow chart illustrating steps for monitoring a landslide event according to an embodiment of the present invention.

Flow chart of a process 500 illustrating steps for monitoring a landslide event according to an embodiment of the present invention is given in FIG. 5. At step 501 a rain event is in progress in one or more deployment fields. At step 502, the system monitors rain gauges. The frequency of monitoring may change based on changes in amounts of rain collected or by rates of rainfall measured by the gauges. In this example, the method used is the sensor-triggered method previously described with reference to FIG. 2 to FIG. 4.

At step 503, the system determines if rainfall is measured above a pre-set threshold for a low-level alert. It is noted in this example that the system is first monitoring the rain gauges and not necessarily the other hydrologic sensors. In this way as long as rainfall amounts are low there is no real need to take measurements from dielectric moisture sensors or the piezometers.

At step 503, if it is determined that rainfall is not above the first preset threshold, the process resolves back to step 502. However, if at step 503 it is determined that rainfall is above the lowest preset threshold for total rainfall amount or rate of rainfall measured per hour, then the system powers on the dielectric moisture sensors at step 504. At step 505, rain gauges and moisture sensors deployed in the various soil layers above and below the water table are monitored. The frequency of monitoring may be increased depending on rainfall amount of the rain gauges. Dielectric moisture sensors are used for measuring moisture levels in the soil.

At step 506 the system determines if a second threshold for saturation of the moisture sensors is breached relative to average saturation level of the sensors or readings from selected sensors. In one aspect, the saturation levels of all of the moisture sensors are averaged relative to a saturation threshold for all of the soil layers and within the borehole. In another aspect the sensor data is aggregated separately and any breach of the threshold by any of the sensors is sufficient to raise the alert level. In still another aspect the dielectric sensors are monitored followed by steps for powering on and monitoring of the piezometers if the threshold for dielectric sensors in the soil levels above the water table are breached. In this case another threshold would be established for the one or more piezometers.

At step 506 if it is determined that the saturation level of the moisture sensors is not above the preset threshold, the process resolves back to step 505. If at step 506 the saturation level is above the preset threshold, the system powers on the piezometers deployed within the wireless node and deep earth probes at step 507. At this point the alert level is raised and the monitoring frequency may be increased. Also, at this point the rain gauges may be monitored still even though they may be all above the preset level for rain gauges and the readings may become static until rainfall rates decline.

At step 508, rain gauges, moisture sensors and piezometers deployed in the various soil layers above and below the water table are monitored. The frequency of monitoring may be increased depending on rainfall amount of the rain gauges. Piezometers are used for measuring water pressure in the borehole both above and below the water table.

At step 509, if it is determined that the pore-pressure values are not above the preset threshold, the process resolves back to step 508. If at step 509 the pore-pressure value is above the preset threshold, the system powers on the movement sensors and geophones deployed with the wireless node and deep earth probes at step 510. At this point the alert level is raised and the monitoring frequency may be increased.

At step 511, the system monitors the geologic sensors including geophones, strain gauges, and tiltmeters in order to detect actual movement of earth associated with an active landslide event. The severity of an impending slide may also be predicted based on preliminary detection of movement by any of the above-mentioned sensors.

The amount of earth movement detected or the rate at which movement is detected measured at the granularity of millimeters may help to classify the severity of the event and may help to predict possible outcomes relative to preliminary damage level predictions. At step 512 the process ends with respect to the flow of the monitoring process. However, monitoring continues until the threat subsides in the event that a slide does not materialize. By utilizing this multi-tiered alert process, persons in the path of the impending landslide will have much more time to evacuate to a safe location than would otherwise be the case. At the same time, less power is consumed by the system and the alert data is more accurate and less redundant.

In another aspect of the invention the inventors have provided a novel, multi-level warning system that incorporates multiple triggering factors (as many as five), reduces the rate of false alarms, and improves efficacy by utilizing dynamic thresholds. This new and novel system is described below in enabling detail with reference to FIGS. 6-10.

Detection and early warning of landslides, a complex, natural phenomena, requires knowledge of spatio-temporal variation of multiple parameters. A cohesive decision model integrating the interrelated variations in the triggering parameters provides a unified decision for early warning of landslides. The landslide early warning model described below, in one embodiment, involves four levels of warning: (1) voting: collaboratively decide among rainfall threshold models for different antecedent conditions derived through multiple models such as intensity duration model, adaptive learning techniques etc.; (2) hierarchical forecasting: integrated decision based on the forecasted subsurface pore pressure through dynamic adaptive machine learning techniques and the rainfall threshold model; (3) hierarchical voting: spatially dispersed pore pressure measurements will be used for determining the real-time factor of safety; and (4) collaborative consensus: real-time measurement and consensus of multi parameters such as rainfall, pore pressure, factor of safety, slope movements and vibrations. A novel aspect is that this is the first of its kind among landslide warning systems, to incorporate more than five triggering factors, reduces false alarms, and improves efficacy by utilizing dynamic thresholds.

Landslides, being one of the deadliest of natural disasters, demands that it is of grave importance to forewarn their occurrence, primarily to safeguard the many thousands of lives that are vulnerable to this hazard. That being said, it is crucial to build a system to early warn impending disaster, which is efficient as well as reliable, so that it serves the purpose without risking people's faith in the system. In order to achieve such a system, it is necessary to take into account the triggering parameters of landslides. Most traditional systems focused only on one or two of those triggering factors, such as rainfall (measured using rain gauges), and surface deformation (using SAR), etc. So, they were not able to bring an effective approach, as they resulted either in generating many false alarms or were not able to give timely warnings. This has motivated a design and development by the present inventors of a Wireless Sensor Network (WSN)/Internet of Things (IoT) based landslide monitoring and detection system, comprising a heterogeneous sensor network which takes into account geological, hydrological and meteorological factors contributing to landslides. This WSN/IoT system is capable of early warning impending disaster through a unique multi-level decision making and early warning module. In various embodiments, the warnings may be issued by sending one or more of an email message, an SMS, flashing a beacon light, or a voice alarm.

Figure 6:
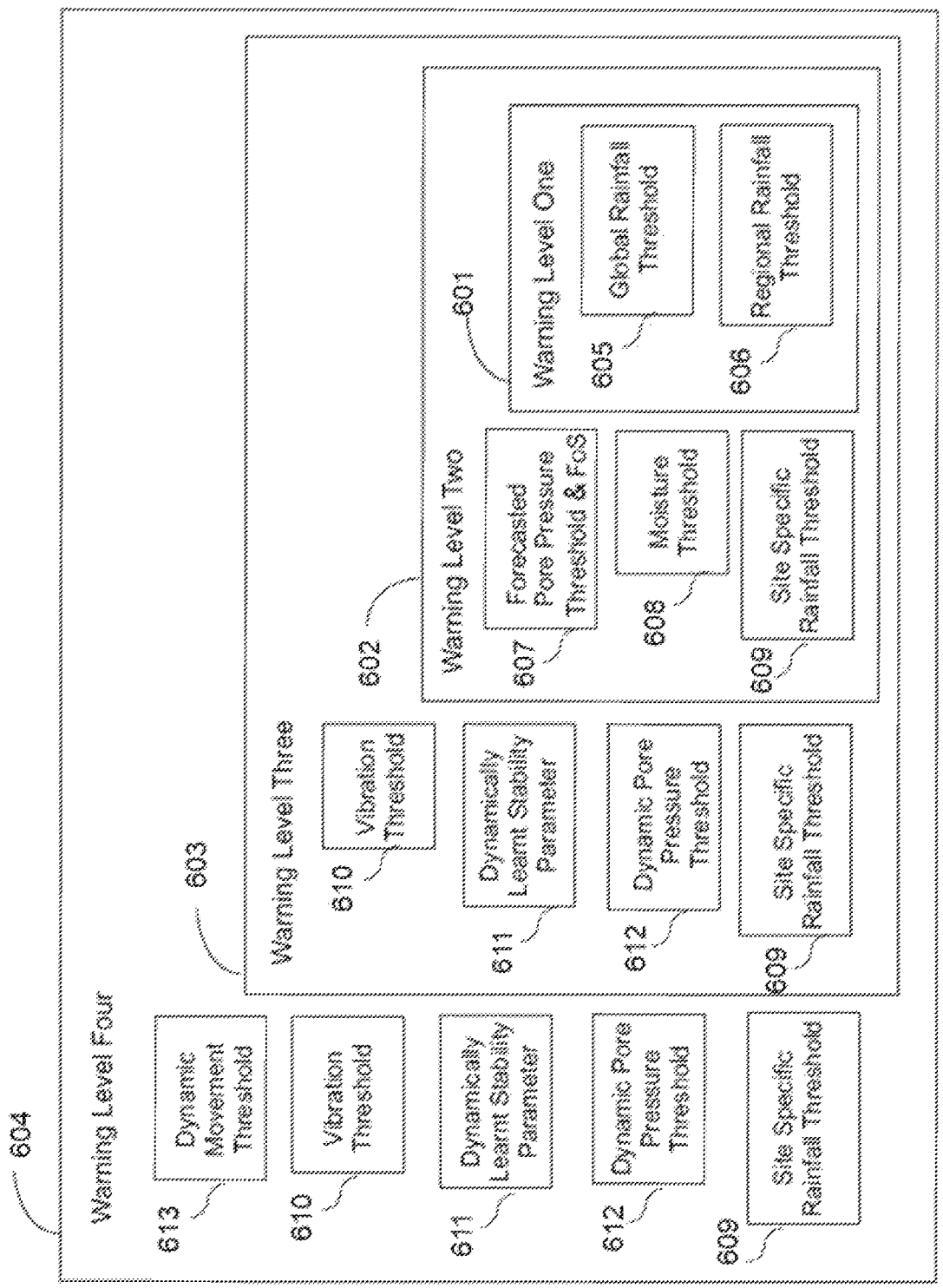
FIG. 6 is a diagram of nested warning levels in one embodiment of the invention.

Variations in triggering factors of landslides, such as rainfall, soil moisture, pore water pressure, ground vibrations & movements, and so on, are captured in embodiments of the present invention in real-time by a heterogeneous sensor network. The sensors in the network correspond to each of the above parameters and are incorporated into a single column called a deep earth probe (DEP), which collects and transmits the real-time sensor data that is being monitored. This real-time data is further assembled, processed and analyzed by a Decision Support System (DSS) that derives decisions pertaining to the landslide warning levels. Exhaustive analysis of this data is performed in a spatio-temporal manner, helping to gain insight into the triggering processes in the study areas, and thereby aided in developing models, which can characterize those processes. The models are integrated into the DSS to facilitate the decision-making process. The DSS adopts a hierarchical, agglomerative clustering approach for generating warnings: starting at a bottom level with rain gauge data and considering the other triggers such as moisture, pore pressure, and movement, including one-by-one as they go up to the higher levels in the warning module. As described above, this not only increases the overall effectiveness of the system, but also reduces the false warning rate due to its dependency on multiple factors for warning generation. As is shown in FIG. 6, these multiple types of data undergo voting or/and consensus mechanisms to provide a unanimous decision concerning a warning at each level. FIGS. 7-10B are detailed flow charts depicting the process for each warning level in the decision model.

First Level Warning: Referring to diagram 601 in FIG. 6, warning level one, labeled element 601 in the decision model uses only rain gauge data, wherein global 605 and regional 606 thresholds for rainfalls for different fixed durations are analyzed, such as 1 hour, 1 day, 3 days, 5 days, 7 days and 15 days of antecedent rainfall. The real-time rainfall data obtained from deployed systems are stored in the database and are converted to rainfall intensity (in mm/hr and mm/day) for these different antecedent durations. The rainfall intensity is then compared with the threshold values for each of those durations, using both global 605 and regional 606 threshold equations. For the global threshold 605, established equations by Caine [Caine, N. (1980). The rainfall intensity-duration control of shallow landslides and debris flows. Geografiskaannaler: series A, physical geography, 62(1-2), 23-27] and Innes [Innes, J. L. (1983). Debris flows. *Progress in physical geography,* 7(4), 469-501] are used. For the regional threshold 606 analysis, threshold equations are used that are provided by the inventors [[3] Harilal, G. T., Madhu, D., Ramesh, M. V., & Pullarkatt, D. (2019). Towards establishing rainfall thresholds for a real-time landslide early warning system in Sikkim, India. Landslides, 16(12), 2395-24082] for the respective regions where deployments are made. The chosen approach in this example considers a voting based on the different durations that leads to the decision, that is, for either the global 605 or regional 606 threshold analysis, if the rainfall intensity has exceeded the threshold 605, 606 for at least three of the above mentioned durations for at least 'T' days, for example, it will issue the first level warning (blue alert). Or, it can also happen in the case where the threshold has crossed for a single duration with the current rainfall intensity being more than a pre-programmed percentage of the threshold value for that duration. The value of the percentage as a threshold depends on climatic/weather conditions prevailing in the study area under consideration. The alert from this level goes only to the researchers or scientists who are the administrators of this system.

Figure 7:
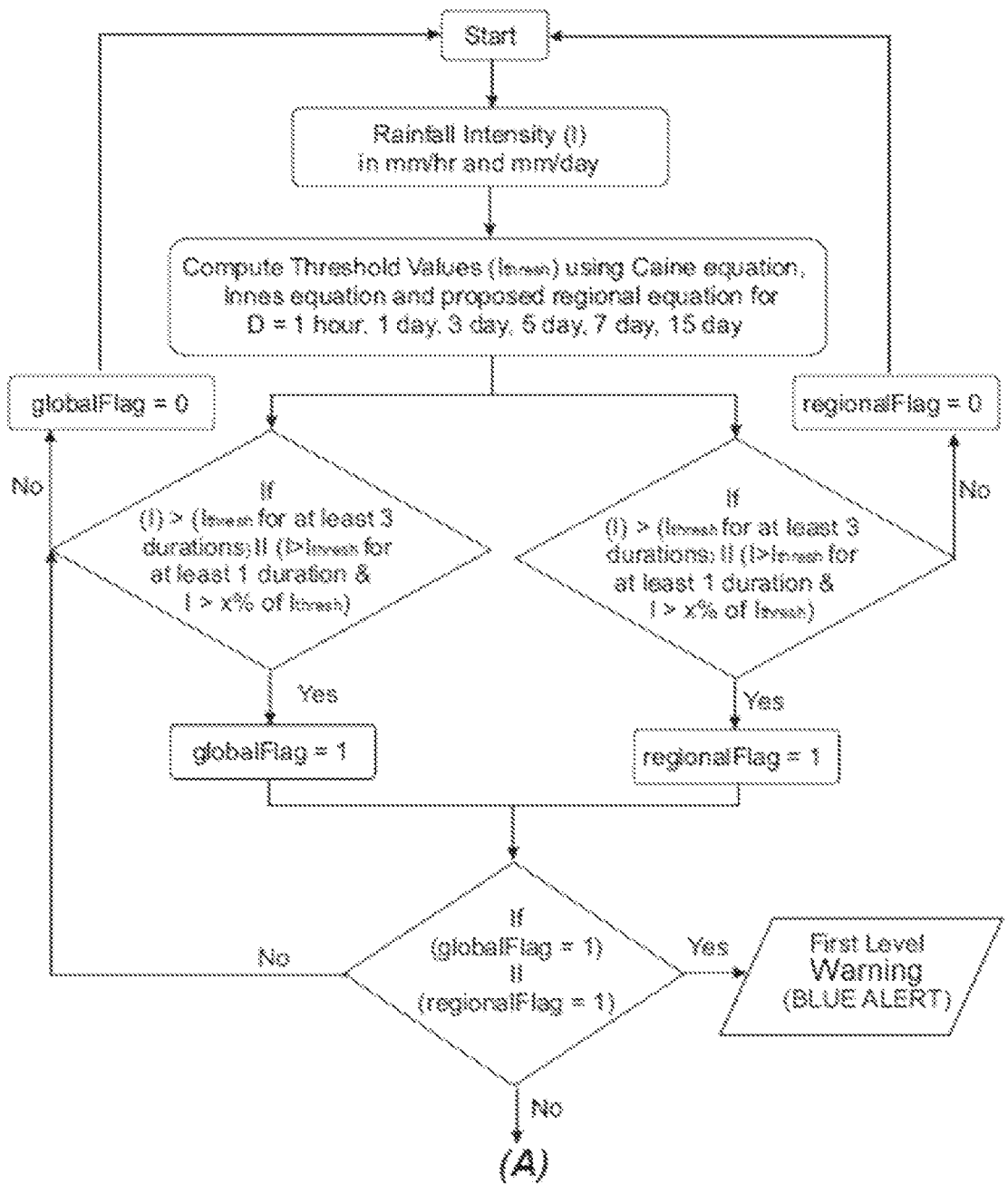
FIG. 7 is a flow diagram illustrating logic in determining a first level warning.

FIG. 7 is a flow chart of the process of issuing warning level one. A start step is shown after which rainfall intensity (I) per hour and per day is calculated. Then Threshold Values ($I_{Thresh}$) for both Global and Regional Rainfall Intensities over several progressively longer Durations (D) from one hour to 15 days are computed. I is compared to $I_{Thresh}$ for the global model. If I is not greater than $I_{Thresh}$ in either case, then the Global flag is set to zero. If I is greater than $I_{Thresh}$ for either case, then the Global flag is set to 1.

I is compared to $I_{Thresh}$ for the regional model. If I is NOT greater than $I_{Thresh}$ in either case, then the Regional flag is set to zero. If, however, I is greater than $I_{Thresh}$ in either case, then the Regional flag is set to one. The Global or Regional flag being set to one results in the First Level alert being issued.

Second Level Warning: A warning level two (second level) illustrated in FIG. 6 as element 602, considers both moisture and pore pressure data in addition to rainfall rate. A major difference from the previous level one is that, from level two onwards, it is a site-specific rainfall threshold equation that is being utilized for decision making. Level two takes a hierarchical forecasting-based approach, wherein the hierarchy is formed by the rainfall in the first level, and moisture and forecasted pore pressure in the second level. Thus, in level two, once the site-specific rainfall threshold 609 is crossed for at least three of the specified durations, continuously for a period of no less than 'T' days, then the moisture threshold 608 and Factor-of-Safety (FoS) 607 values are examined simultaneously. The soil moisture data in VWC (volumetric water content) is constantly compared against the threshold value to check if a state of saturation is approached. Historic pore pressure data and rainfall data is analyzed and utilized by the adaptive learning algorithm for deriving patterns relating the rainfall and pore pressure data. Based on these learnings, by taking the inputs, such as the real-time rainfall data and the soil properties of the location at which the pore-pressure sensors are deployed, the algorithm is able to forecast the pore pressure value 24 hours beforehand. In the case of absence of real-time data due to any unexpected errors, the model exploits the estimated rain data from the weather forecasts for estimating the pore-pressure forecasts. The forecasted pore pressure is then used to compute the resultant FoS values 607 for each location (location here refers to the specific depth and DEP location at which the sensors are deployed). The term FoS represents the stability conditions of the slope; if the FoS value is greater than 1 then the slope is stable and if it is less than 1, then the slope is considered to be susceptible to failure. If the moisture value reaches the saturation level by the threshold getting crossed for multiple locations AND the FoS value falls below 1 for multiple locations or for the vulnerable soil layers, then the second level (yellow alert) warning is issued, and the decision model moves into the next stage. From this level onwards in one embodiment, the alert is provided to government authorities and also such as the district collector.

Figure 8:
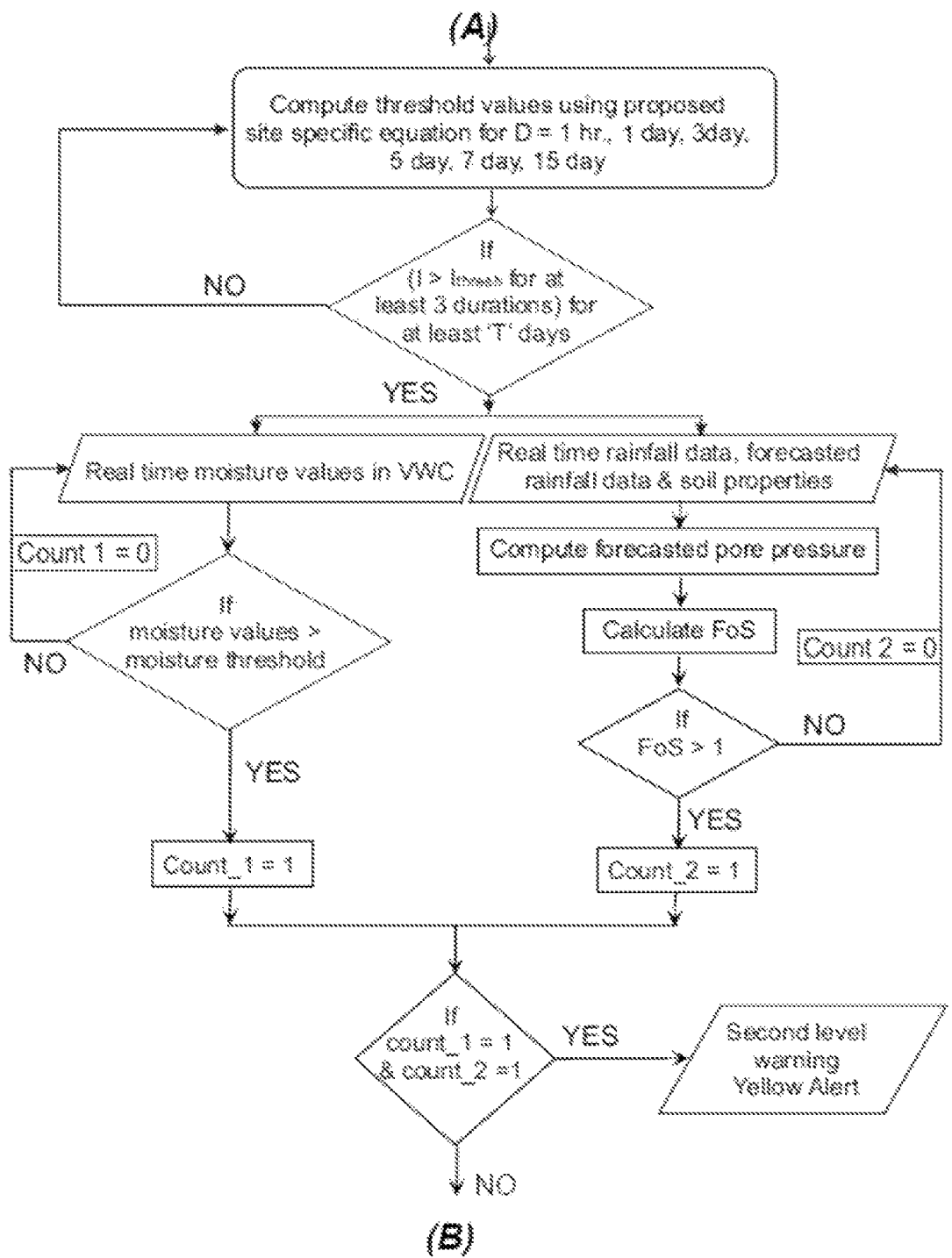
FIG. 8 is a flow diagram illustrating logic in determining a second level warning.

FIG. 8 is a flow chart following from the flow chart of FIG. 7, depicting the process of determining and issuing a Second Level Alert. The process starts with computing threshold values and ends with issuing the Second Level Alert. The detailed logic is illustrated in FIG. 8.

Third Level Warning: A hierarchical voting-based scheme is adopted in the third level 603 of this warning model, as further illustrated with reference to FIGS. 9A and 9B. In this level multiple criteria are considered for generating the warning decision. In one embodiment these levels are: i) the rainfall intensity comparison based on the site-specific threshold 609 ii) the real-time pore water pressure data 612 comparison against the corresponding thresholds and, iii) the threshold comparison for the movement sensor's data 610, 611. The hierarchy here refers to the assessment of the individual sensor values for the above parameters simultaneously in the first tier and then the assessment based on the combination of the values in the next tier. As in the previous warning level 602, here also the site-specific rainfall threshold 609 comparison is conducted to see if it crosses for at least three of the specified durations, continuously for a period of no less than 'T' days and a count will be set if this condition is met. For each DEP location 'l' and depth 'd', the pore-pressure value 612 is compared against the corresponding threshold and for every $i^{th}$ sensor for which the threshold has crossed, the flag value $F_i$ is set as 1. According to the soil properties and other factors, the vulnerability of each location of the slope varies. Hence, weights ($W_i$) are assigned to each of those sensors at these particular locations based on the vulnerability index. The total weight for the slope is then computed using the equation, $W=\Sigma_{i=0}^{n} W_iF_i$, for all the 'n' sensors deployed in that particular study area. Considering the vulnerable layers and other factors, a threshold ($W_{Thresh}$) for the total weight of the slope is computed, which is compared with 'W' and if found crossed, a count value will be incremented.

Figure 9A:
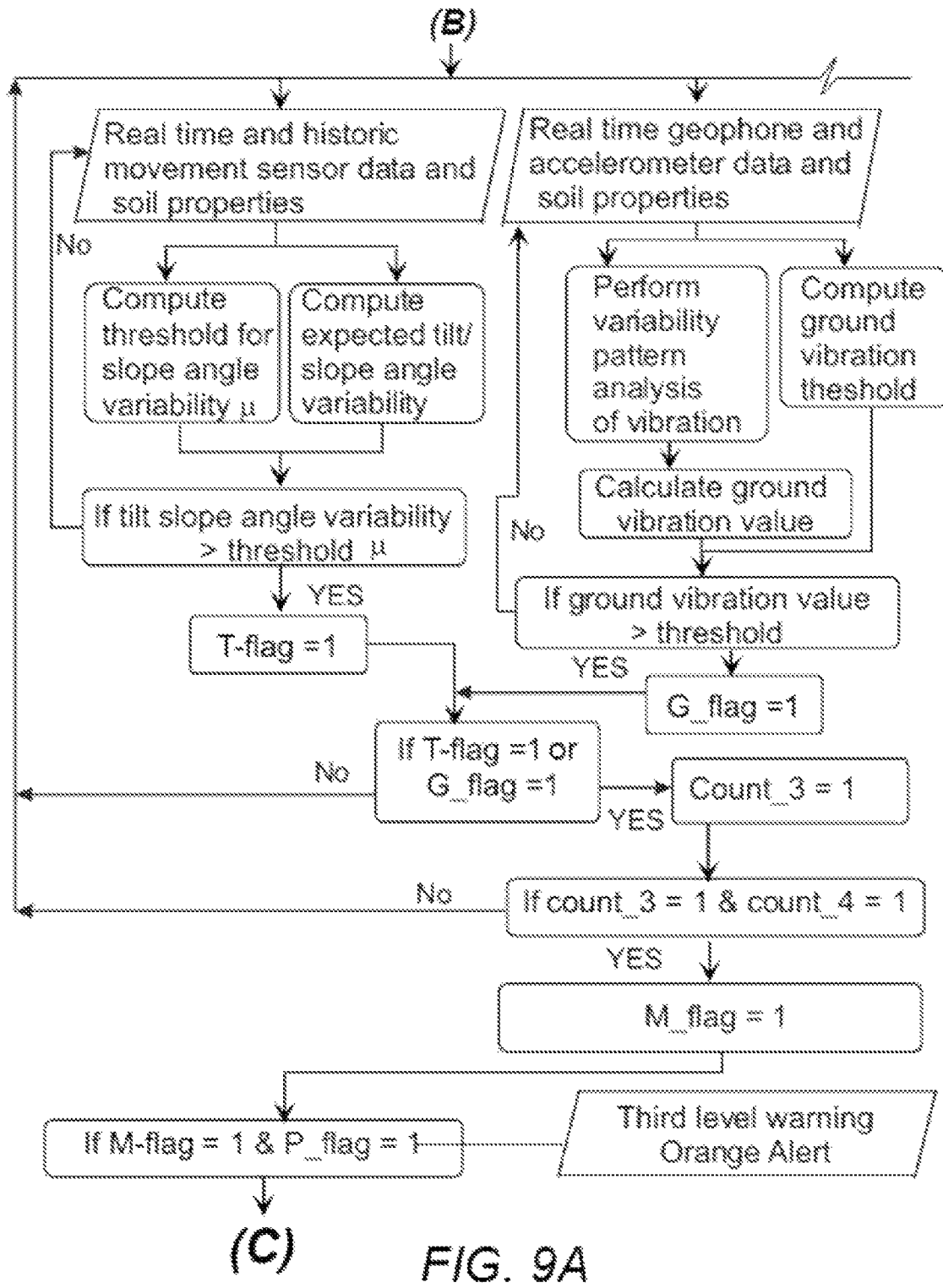
FIGS. 9A and 9B are flow diagrams illustrating logic in issuing a third level warning.
Figure 9B:
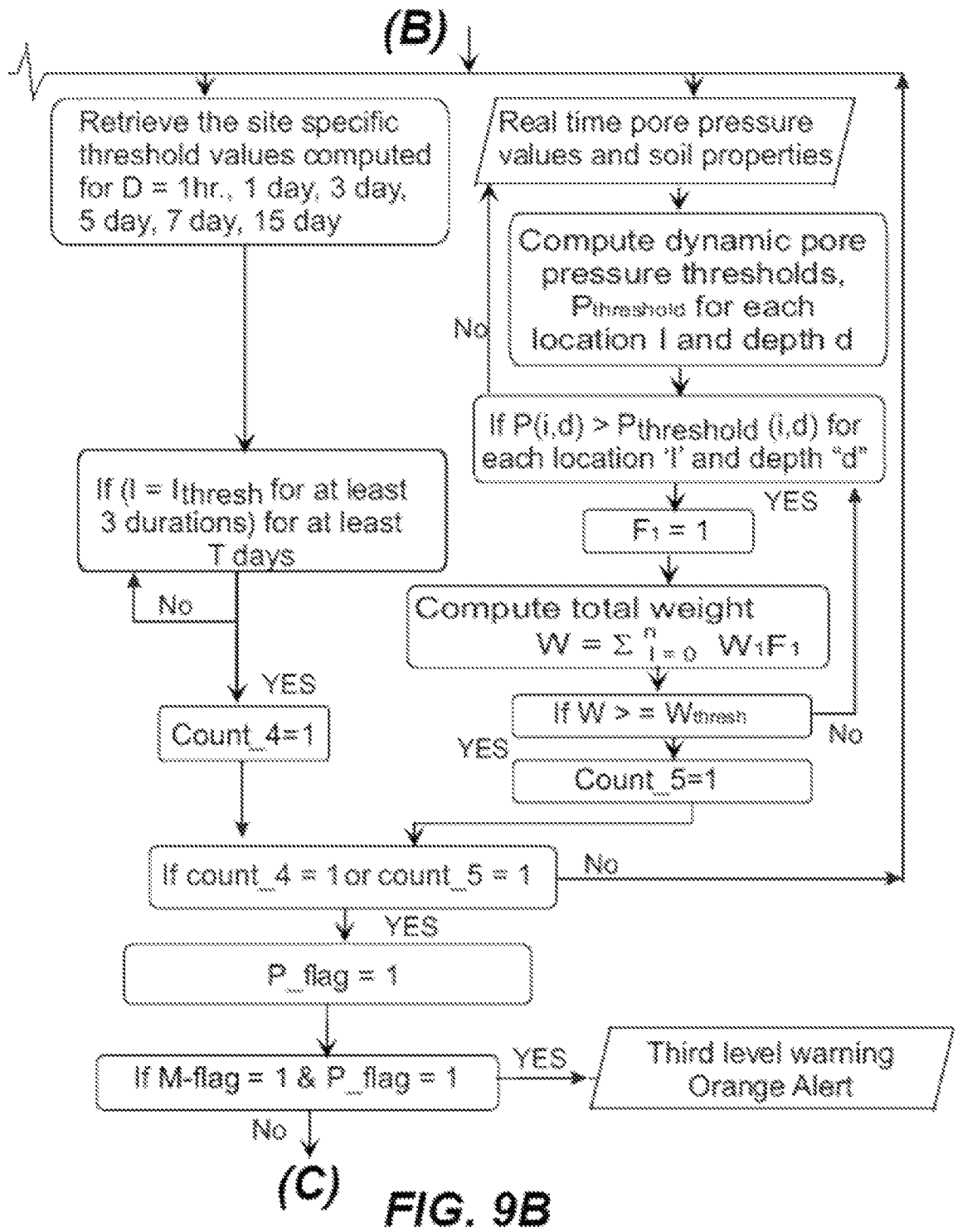

Along with rainfall and pore-pressure based evaluations, data from movement sensors, such as tilt meter and geophone, are also assessed concurrently. Based on the adaptive learning techniques employed, the real-time geophone data and soil properties are utilized to perform variability pattern analysis of the ground vibrations, as illustrated in FIGS. 9A and 9B. Computed ground vibration values are then checked relative to the corresponding threshold 610. Similarly, an expected tilt/slope angle variability is determined using the historic tiltmeter/inclinometer data and soil properties and compared against the threshold value 611. A count value is incremented if either the vibration or tilt value is observed to be crossing their corresponding thresholds. As mentioned above, the next tier of this level uses a combination of the results from the comparisons made in the first tier to arrive at a final decision. If either the count value for the rainfall OR count value for the pore-pressure sensors is obtained as 1, then a flag (P_flag) is set as 1. Or else, if the count value for the movement sensors AND count value for the rainfall sensor is obtained as 1, then another flag (M_flag) is set as 1. Hence, in the third level, if both the M_flag AND the P_flag has acquired value 1, then the third level warning (orange alert) is issued, using the detailed logic as provided in FIGS. 9A and 9B.

Fourth Level Warning: The fourth 604 and the final level alert or warning is mainly based on a collaborative consensus formed by the rainfall sensors, pore-pressure sensors and movement-based sensors, such as strain gauges, tilt-meters and geophones, as further illustrated with reference to FIGS. 10A and 10B. Results from the movement sensors are a crucial element here as these sensors are able to capture sub-surface movements, which result in slides. Based on the context, the adaptive learning algorithms derive dynamically learnt stability parameters based on the movement sensor data which accounts for the dynamic changes in geological parameters with respect to time, and also compute the dynamic thresholds for the pore pressures as well.

In addition to the geophone and tilt-meter-data based assessments performed in the third level 603, the fourth level 604 also considers strain gauge data for decision generation from the movement sensors. The Strain Gauge-based movement sensor is a custom sensor developed with an aim to reduce cost of the overall installation of the system. Data from these sensors is interpreted and converted to microstrains. The converted micro-strain data is further processed to determine strain rate and current state of stress at different depths by applying models from theory of soil mechanics. Now the derived values of these parameters are compared against the measured maxima of these parameters and a count value is incremented if it crosses the set threshold 613.

Figure 10A:
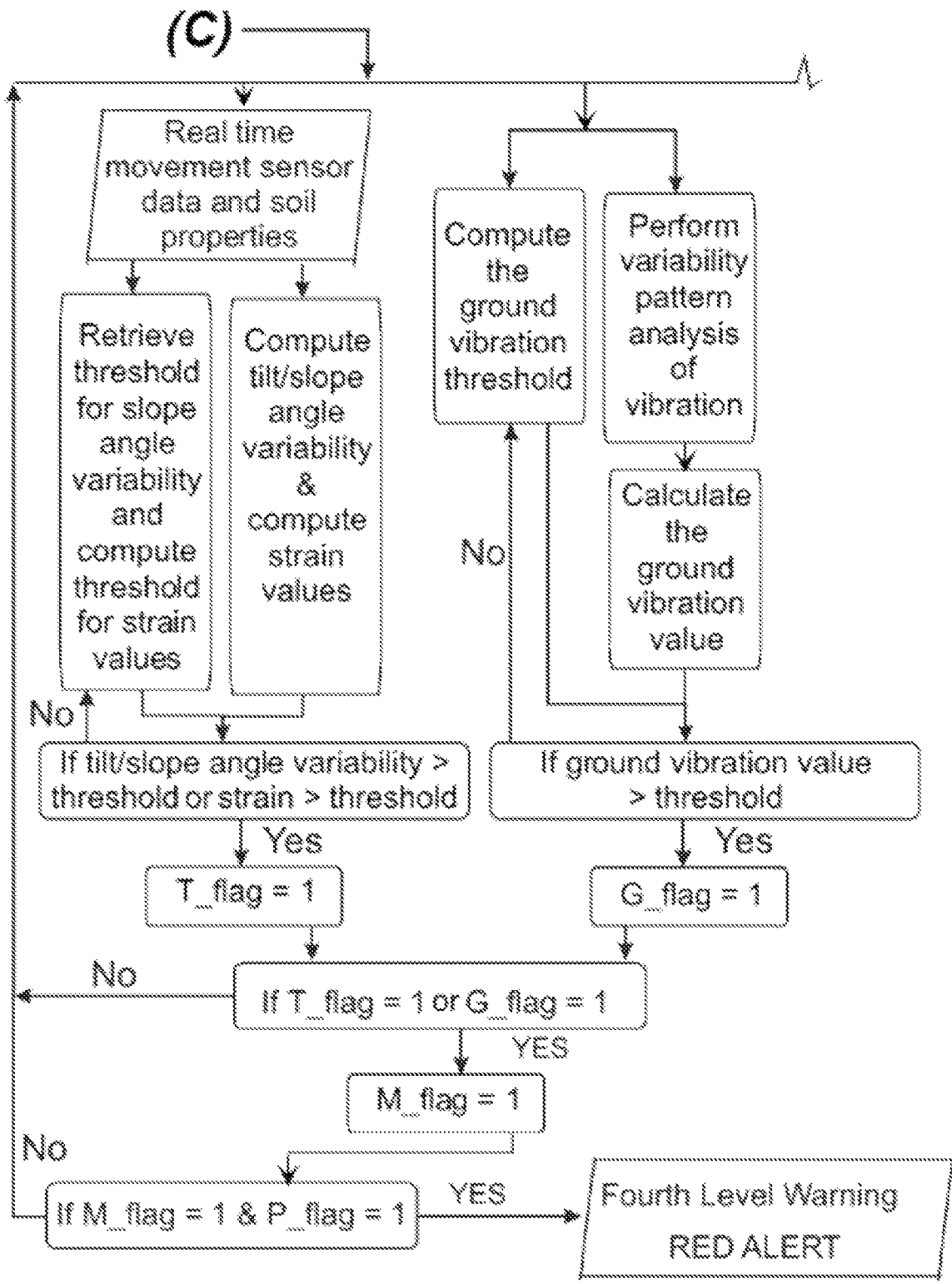
FIGS. 10A and 10B are flow diagrams illustrating logic in issuing a fourth level warning.
Figure 10B:
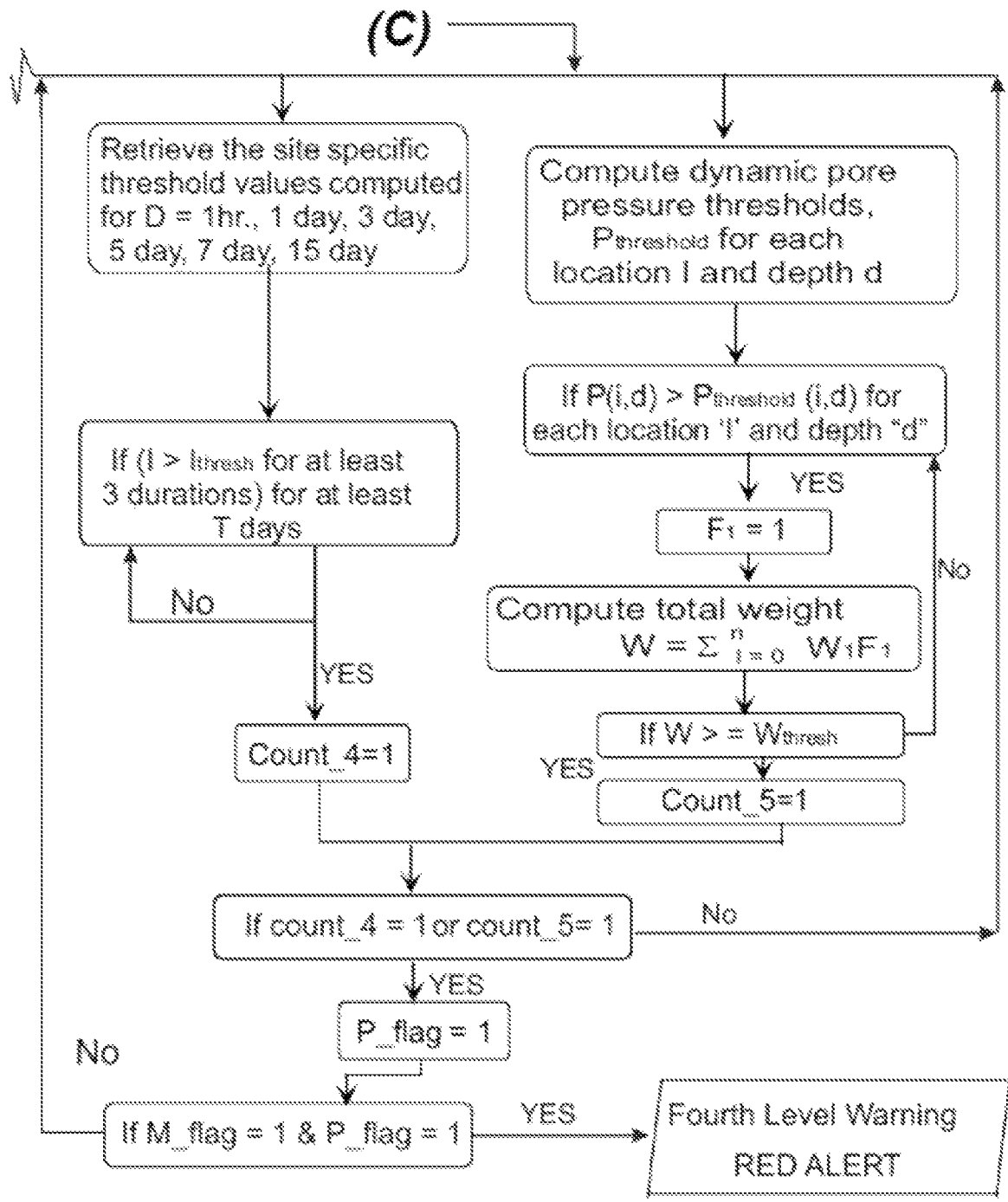

The site-specific rainfall threshold 609 comparison is repeated in this level also. The pore-pressure-based assessment follows the same methodology as in the previous level 603, by comparing real time pore pressure values. Finally, after obtaining results for individual sensor-based assessments, the rainfall 609, pore-pressure 612 and movement sensor arrives at a consensus depending on flags that have been set. If either the count value for the rainfall OR count value for the pore-pressure sensors is obtained as 1, then a flag (P_flag) is set as 1. Or else, if the count value for the tiltmeter/strain gauge sensors OR count value for the ground vibration sensors is obtained as 1, then another flag (M_flag) is set as 1. Hence, in the third level 603, if both the M_flag AND the P_flag have acquired value 1, then the fourth level warning (red alert) is issued, as shown in FIGS. 10A and 10B.

In various embodiments of the claimed method, the warnings may be issued using various means. The warnings may comprise issuing the first level warning, second level warning, third level warning, or fourth level through actuating one or more of an email message, an SMS, a flashing light, or a voice alarm. The multi-level landslide early warning model in embodiments of the invention integrates multiple parameters which influence the geological, hydrological, and meteorological conditions of the study site based on which the decisions pertaining to the landslide forecast are generated. The real-world deployments based on WSN/IoT have extended the scope of this model beyond that of theoretical/simulation-based models.

It will be apparent to the skilled artisan that the landslide prediction system of the invention may be provided using some or all of the mentioned features and components without departing from the scope of the present invention. It will also be apparent to the skilled artisan that the embodiments described above are specific examples of a single broader invention that may have greater scope than any of the singular descriptions taught. There may be many alterations made in the descriptions without departing from the scope of the present invention. The scope is limited only by the claims below.

We claim:

1. A hierarchical early-warning method for determining probability of a landslide, comprising:
   determining rainfall intensity per hour and per day for antecedent durations from one hour up to fifteen days, determining threshold values for a global model and a regional model, comparing intensity to threshold value for each model, and issuing a first level warning if either threshold is exceeded;
   issuing a second level warning, after the first level warning, based additionally on soil moisture content measured at different levels, and calculated factor of safety (FoS) determined using forecasted pore pressure (FPP), each exceeding a determined threshold;
   issuing a third level warning, after the first and the second level warnings, based additionally on real-time pore-pressure measurements and ground movement measurements compared to a determined threshold; and
   issuing a fourth level warning after the first, second and third level warnings, based additionally on data from movement-based sensors including strain gauge data.

2. The method of claim 1 wherein, in the determination of the first level warning, a global and a regional threshold are determined and compared to rainfall intensity calculated from the measured rainfall.

3. The method of claim 1 wherein, in determination of the second level warning, threshold values are determined for progressively longer durations from one hour to fifteen days.

4. The method of claim 1 wherein, in determination of the second level warning, a site-specific rainfall threshold is determined to have been exceeded, in addition to thresholds for Factor of Safety and moisture content.

5. The method of claim 1 wherein, in determination of the third level warning, ground movement measurements include vibration intensity.

6. The method of claim 1 wherein, issuing the first level warning, second level warning, third level warning, or fourth level warning, comprises actuating one or more of an email message, an SMS, a flashing light, or a voice alarm.

7. A hierarchical early-warning method for determining probability of a landslide, comprising:
   issuing a first level warning based on measured rainfall amounts exceeding a determined threshold;
   issuing a second level warning, after the first level warning, based additionally on soil moisture content measured at different levels, and calculated factor of safety (FoS) determined using forecasted pore pressure (FPP), each exceeding a determined threshold;
   issuing a third level warning, after the first and the second level warnings, based additionally on real-time pore-pressure measurements and ground movement measurements compared to a determined threshold; and
   issuing a fourth level warning after the first, second and third level warnings, based additionally on data from movement-based sensors including strain gauge data;
   wherein, in determination of the second level warning, a Factor of Safety (FoS) value, indicating stability of a slope in consideration, is calculated based in part on forecasted pore pressure, and Volumetric Water Content (VWC) is measured using DMS (Dielectric Moisture Sensor), and the second level warning is issued if both the measured VWC goes beyond the set threshold, meaning the soil is saturated, and the FoS is less than one, meaning the slope is unstable.

8. A hierarchical early-warning method for determining probability of a landslide, comprising:
   issuing a first level warning based on measured rainfall amounts exceeding a determined threshold;
   issuing a second level warning, after the first level warning, based additionally on soil moisture content measured at different levels, and calculated factor of safety (FoS) determined using forecasted pore pressure (FPP), each exceeding a determined threshold;
   issuing a third level warning, after the first and the second level warnings, based additionally on real-time pore-pressure measurements and ground movement measurements compared to a determined threshold; and
   issuing a fourth level warning after the first, second and third level warnings, based additionally on data from movement-based sensors including strain gauge data;
   wherein, in determination of the fourth level warning, four parallel logical paths are followed, a first comparing rainfall intensity to site-specific threshold, a second based on measured tiltmeter data, measured strain gauge data and soil properties, a third based on geophone data and soil properties, and a fourth based on measured pore pressure and weighted location-specific threshold values.

* * * * *